(12) United States Patent
Otsubo et al.

(10) Patent No.: US 10,624,684 B2
(45) Date of Patent: Apr. 21, 2020

(54) SPINAL FIXATION HOLDING DEVICE AND SPINAL FIXATION SYSTEM HAVING THE SAME

(71) Applicant: TEIJIN NAKASHIMA MEDICAL CO., LTD., Okayama (JP)

(72) Inventors: Masato Otsubo, Kanagawa (JP); Tobimaru Takata, Tokyo (JP); Yuichi Sato, Kanagawa (JP)

(73) Assignee: TEIJIN NAKASHIMA MEDICAL CO., LTD., Okayama (JP)

( * ) Notice: Subject to any disclaimer, the term of this patent is extended or adjusted under 35 U.S.C. 154(b) by 107 days.

(21) Appl. No.: 15/763,930

(22) PCT Filed: Sep. 28, 2015

(86) PCT No.: PCT/JP2015/004910
§ 371 (c)(1),
(2) Date: Mar. 28, 2018

(87) PCT Pub. No.: WO2017/056125
PCT Pub. Date: Apr. 6, 2017

(65) Prior Publication Data
US 2018/0353223 A1 Dec. 13, 2018

(51) Int. Cl.
*A61B 17/70* (2006.01)
*A61B 90/00* (2016.01)
*A61B 17/68* (2006.01)

(52) U.S. Cl.
CPC ........ *A61B 17/7082* (2013.01); *A61B 17/708* (2013.01); *A61B 17/7085* (2013.01);
(Continued)

(58) Field of Classification Search
CPC ............................. A61B 17/70; A61B 17/7082
See application file for complete search history.

(56) References Cited

U.S. PATENT DOCUMENTS

| | | | |
|---|---|---|---|
| 2008/0275456 A1* | 11/2008 | Vonwiller | A61B 17/7032 606/246 |
| 2014/0277206 A1* | 9/2014 | Reitblat | A61B 17/708 606/86 A |
| 2015/0148849 A1* | 5/2015 | Abidin | A61B 17/708 606/279 |

FOREIGN PATENT DOCUMENTS

| | | |
|---|---|---|
| JP | 2010-525874 A | 7/2010 |
| JP | 2014-176705 A | 9/2014 |

OTHER PUBLICATIONS

International Search Report issued in PCT Patent Application No. PCT/JP2015/004910 dated Oct. 27, 2015.
(Continued)

*Primary Examiner* — Christopher J Beccia
(74) *Attorney, Agent, or Firm* — Marshall, Gerstein & Borun LLP (57) ABSTRACT

A holding device includes a cylindrical main body portion having an outer cross-section equal to or less than a cross-section defining the inner wall of an upper portion and a pair of locking pieces protruding outward from the distal end portion of the main body portion in the direction of the central axis along a direction perpendicular to the central axis at the positions of a pair of slots while the main body portion is positioned within the inner wall of the upper portion when viewed from the direction of the central axis. The pair of locking pieces have such a shape as to be contained within the outer shape of the head portion while being positioned within the pair of slots.

5 Claims, 9 Drawing Sheets

(52) U.S. Cl.
CPC ....... *A61B 17/7037* (2013.01); *A61B 17/7091* (2013.01); *A61B 2017/681* (2013.01); *A61B 2090/037* (2016.02)

(56) References Cited

OTHER PUBLICATIONS

Written Opinion of the International Searching Authority issued in PCT Patent Application No. PCT/JP2015/004910 dated Oct. 27, 2015.

* cited by examiner

SPINAL FIXATION HOLDING DEVICE AND SPINAL FIXATION SYSTEM HAVING THE SAME

TECHNICAL FIELD

The present invention relates to a spinal fixation holding device and a spinal fixation system having the same.

BACKGROUND ART

Spinal fusion surgery is known, in which spacings between a plurality of vertebrae are held, a spinal fixation tool such as a spinal screw is engaged with each vertebra to relax the pressure on the nerve, and a plurality of spinal fixation tools are coupled to each other with rod members. There is known a mode of attaching a spinal fixation holding device to the proximal end portion (head portion) of each spinal fixation tool to hold the spinal fixation tool, used for such spinal fusion surgery, when fixing the spinal fixation tool to the vertebra (see, for example, PTL 1).

CITATION LIST

Patent Literature

PTL 1: Japanese Unexamined Patent Publication No. 2014-176705

SUMMARY OF INVENTION

Technical Problem

However, because the conventional holding device as disclosed in PTL 1 engages with a groove or the like formed in the outer peripheral surface of the head portion of each spinal fixation tool so as to grip it from outside, the maximum diameter (maximum width) of the entire device after the holding device is engaged with the spinal fixation tool becomes undesirably larger than the maximum diameter (maximum width) of the spinal fixation tool.

Because spinal fixation tools are invasively installed in the body of the subject by incision, an increase in the maximum diameter of the entire device will increase the range of invasion into the human body. This will increase the burden on the human body.

The present invention has been made to solve the above problems and an object thereof is to provide a spinal fixation holding device that can prevent an increase in the range of invasion into a human body when the holding device is attached to each spinal fixation tool and a spinal fixation system having the spinal fixation holding device.

Solution to Problem

A spinal fixation tool holding device according to one aspect of the present invention is a spinal fixation tool holding device for holding a spinal fixation tool. The spinal fixation tool includes a bone engagement portion provided at a distal end portion and engaged with a bone, and a head portion provided at a proximal end portion. The head portion has a cylindrical lower portion that holds the bone engagement portion, and an upper portion extending upward from the lower portion and having an outer wall and an inner wall having an identical central axis to a central axis of an outer shape of the lower portion. The upper portion has a pair of slots which are opened in a direction perpendicular to the central axis in parts of the outer wall and the inner wall around the central axis. The holding device includes a cylindrical main body portion having an outer cross-section equal to or less than a cross-section defining the inner wall of the upper portion, and a pair of locking pieces protruding outward from the distal end portion of the main body portion in the central axis direction along a direction perpendicular to the central axis at the pair of slot positions while the main body portion is positioned within the inner wall of the upper portion when viewed from the central axial direction. The pair of locking pieces have engagement portions that are engaged with side walls joining the outer wall and the inner wall of the head portion and/or a rod member held by the pair of slots while being positioned inside the pair of slots. The pair of locking pieces each have such a shape as to be contained within the outer shape of the head portion while being positioned within the pair of slots.

According to the above configuration, while the main body portion of the holding device is positioned inside the head portion of the spinal fixation tool, the pair of locking pieces exist at the pair of slot positions on the head portion so as to protrude outward from the main body portion along a direction perpendicular to the central axis. Accordingly, the engagement portions of the pair of locking pieces are engaged with the head portion and/or the rod member held by the head portion. At this time, the pair of locking pieces protruding into the pair of slots each have such a shape as to be contained within the outer shape of the head portion while being positioned within the pair of slots. Therefore, when the holding device is engaged with the head portion of the spinal fixation tool to hold the spinal fixation tool, the holding device is prevented from protruding from the spinal fixation tool. This can prevent an increase in the range of invasion into the human body when the holding device is attached to the spinal fixation tool.

The engagement portions may be formed on both end portions of each of the pair of locking pieces in the widthwise direction, and each of the pair of the locking pieces may have a width corresponding to a width of each of the pair of slots of the head portion. In this case, both end portions of each of the pair of locking pieces in the widthwise direction are engaged with a portion defining a pair of slots of the head portion. Accordingly, holding the holding device will prevent the spinal fixation tool from pivoting in the circumferential direction.

The engagement portion may have an arcuate notch corresponding to the outer diameter of the rod member at the distal end portion of each of the pair of locking pieces. In this case, the respective distal end portions of the pair of locking pieces are engaged with the rod member held in the pair of slots of the head portion. Therefore, holding the holding device will prevent the spinal fixation tool holding the rod member from pivoting in the circumferential direction.

The spinal fixation tool may have a pair of tab portions extending in a central axis direction from a distal end portion of the upper portion of the head portion in the central axis direction. The holding device may be positioned between the pair of tab portions in a state where the pair of locking pieces are engaged with the side wall of the head portion or the rod member.

A spinal fixation system according to another aspect of the present invention is a spinal fixation system including a spinal fixation tool and a spinal fixation holding device for holding the spinal fixation tool. The spinal fixation tool includes a bone engagement portion provided at a distal end portion and engaged with a bone, and a head portion provided at a proximal end portion. The head portion has a cylindrical lower portion that holds the bone engagement portion, and an upper portion extending upward from the lower portion and having an outer wall and an inner wall having an identical central axis to a central axis of an outer shape of the lower portion. The upper portion has a pair of slots which are opened in a direction perpendicular to the central axis in parts of the outer wall and the inner wall around the central axis. The holding device includes a cylindrical main body portion having an outer cross-section equal to or less than a cross-section defining the inner wall of the upper portion, and a pair of locking pieces protruding outward from the distal end portion of the main body portion in the central axis direction along a direction perpendicular to the central axis at the pair of slot positions while the main body portion is positioned within the inner wall of the upper portion when viewed from the central axial direction. The pair of locking pieces have side walls of the head portion while being positioned inside the pair of slots and/or engagement portions that are engaged with a rod member held by the pair of slots. The pair of locking pieces each have such a shape as to be contained within the outer shape of the head portion while being positioned within the pair of slots.

The above object and other objects, features, and advantages of the present invention will become apparent from the following detailed description of the preferred embodiment with reference to the accompanying drawings.

Advantageous Effects of Invention

The present invention is configured as described above, and has an effect of preventing an increase in the range of invasion into the human body when attaching a holding device to a spinal fixation tool.

DESCRIPTION OF EMBODIMENTS

Hereinafter, preferred embodiments of the present invention will be described with reference to the accompanying drawings. In the following description, the same or equivalent elements are denoted by the same reference numerals throughout the drawings, and a repetitive description will be omitted. In the description of the specification and the scope of claims, the "upward" direction and the "downward" direction are determined based on the orientation of the spinal fixation tool at the time of an operation for the human body. That is, the side close to the spine is defined as the lower side, whereas the side far from the spine is defined as the upper side.

Figure 1:
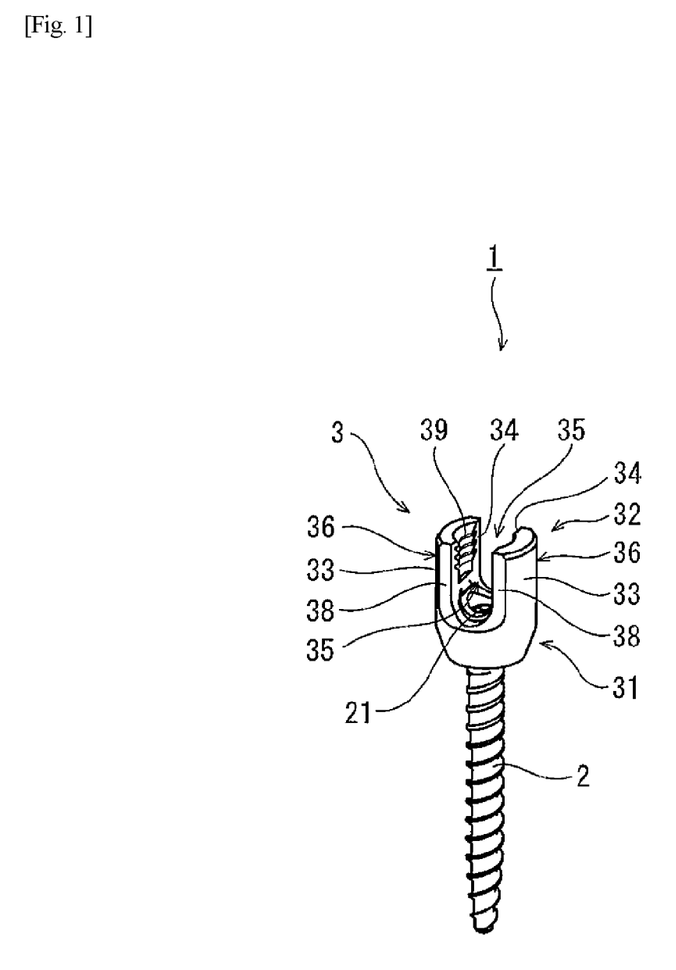
FIG. 1 is a perspective view showing an example of a spinal fixation tool to which a spinal fixation tool holding device according to an embodiment of the present invention can be applied.

A spinal fixation tool according to this embodiment will be described first. FIG. 1 is a perspective view showing an example of a spinal fixation tool to which a spinal fixation tool holding device according to an embodiment of the present invention can be applied. As shown in FIG. 1, a spinal fixation tool 1 includes a bone engagement portion 2 provided at a distal end portion and engaged with a bone such as a vertebrae, and a head portion 3 provided at a proximal end portion. In the example shown in FIG. 1, the bone engagement portion 2 is configured as a screw shaft having a threaded portion to be threadably engaged with a bone such as a vertebra.

The bone engagement portion 2 is held so as to be relatively rotatable in the axis line direction with respect to the head portion 3. A driver engagement portion 21 is formed at the proximal end portion of the bone engagement portion 2 in an upward direction. The driver engagement portion 21 has a groove in the shape of a plus sign, minus sign, hexagon, or star. Accordingly, a driver (not shown) having a convex shape corresponding to the groove of the driver engagement portion 21 is engaged with the driver engagement portion 21 while holding the head portion 3, and the bone engagement portion 2 can be relatively rotated with respect to the head portion 3 by rotating the driver about the axis line. This makes it possible to engage the bone engagement portion 2 with a predetermined vertebra or to cancel the engagement.

The head portion 3 includes a circular cylindrical lower portion 31 for holding the bone engagement portion 2 and an upper portion 32 extending upward from the lower portion 31. The circular cylindrical portion forming the outer periphery of the lower portion 31 includes a portion that defines the maximum diameter of the head portion 3 (an outer circumferential circle C1 centered on the central axis C0 in FIG. 5 described later).

Figure 5:
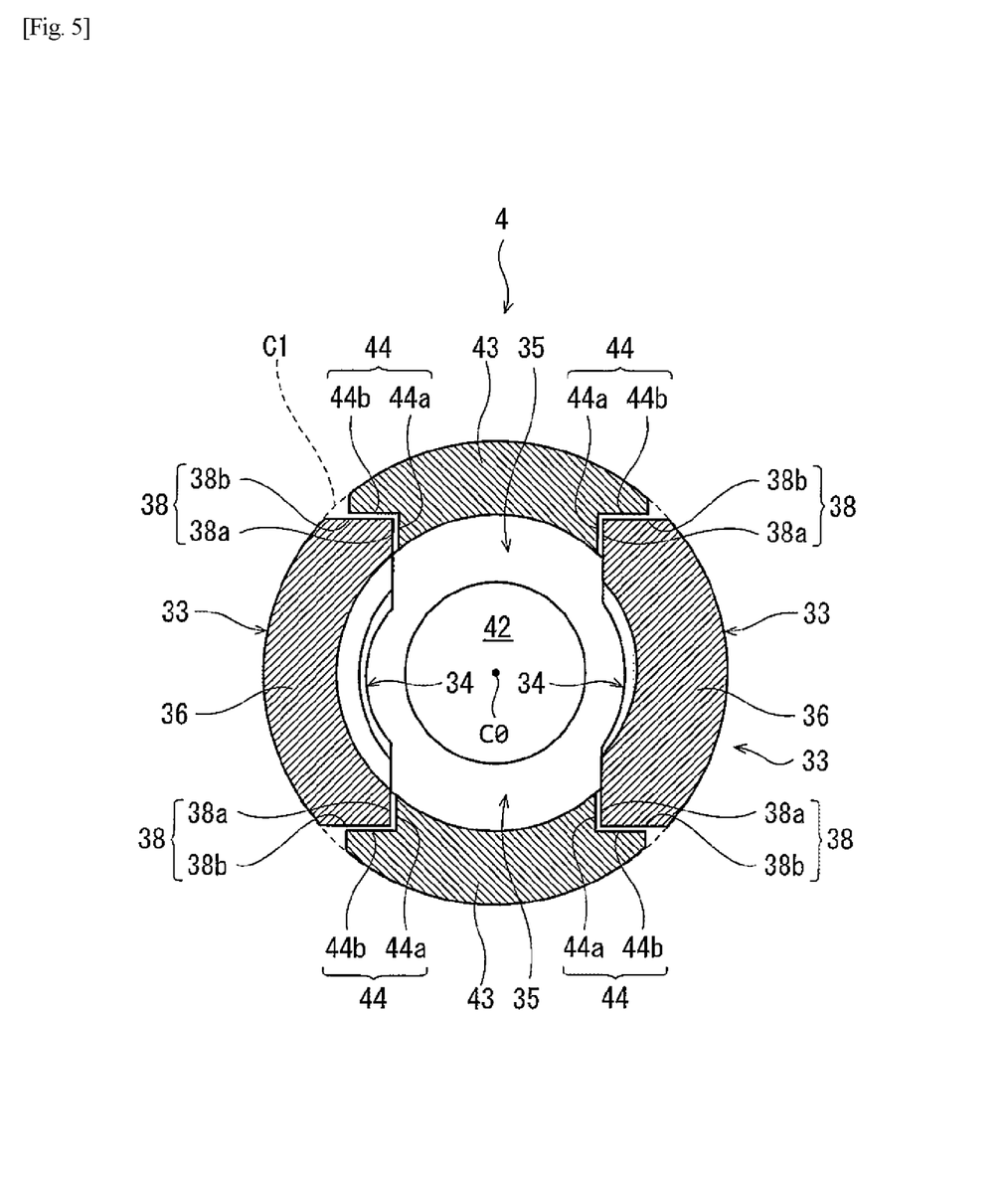
FIG. 5 is a cross-sectional view taken along line V-V shown in FIG. 4.

The upper portion 32 has an outer wall 33 and an inner wall 34 formed concentrically with the outer circumferential circle of the lower portion 31. Furthermore, the upper portion 32 has a side wall 38 joining the outer wall 33 to the inner wall 34. In the upper portion 32, a pair of slots 35 opened in the radial direction are formed in parts of the outer wall 33 and the inner wall 34 in the circumferential direction. The pair of slots 35 are formed such that the upper end portion of the upper portion 32 is opened and the lower end portion has an arcuate shape. The upper portion 32 is formed by the pair of slots 35 so as to have a pair of arcuate portions 36 facing each other and extending upward from the lower portion 31.

In this embodiment, the outer circumferential circle defining the outer wall 33 of the upper portion 32 has the same diameter as that of the outer circumferential circle C1 that defines the maximum diameter of the lower portion 31.

Figure 2:
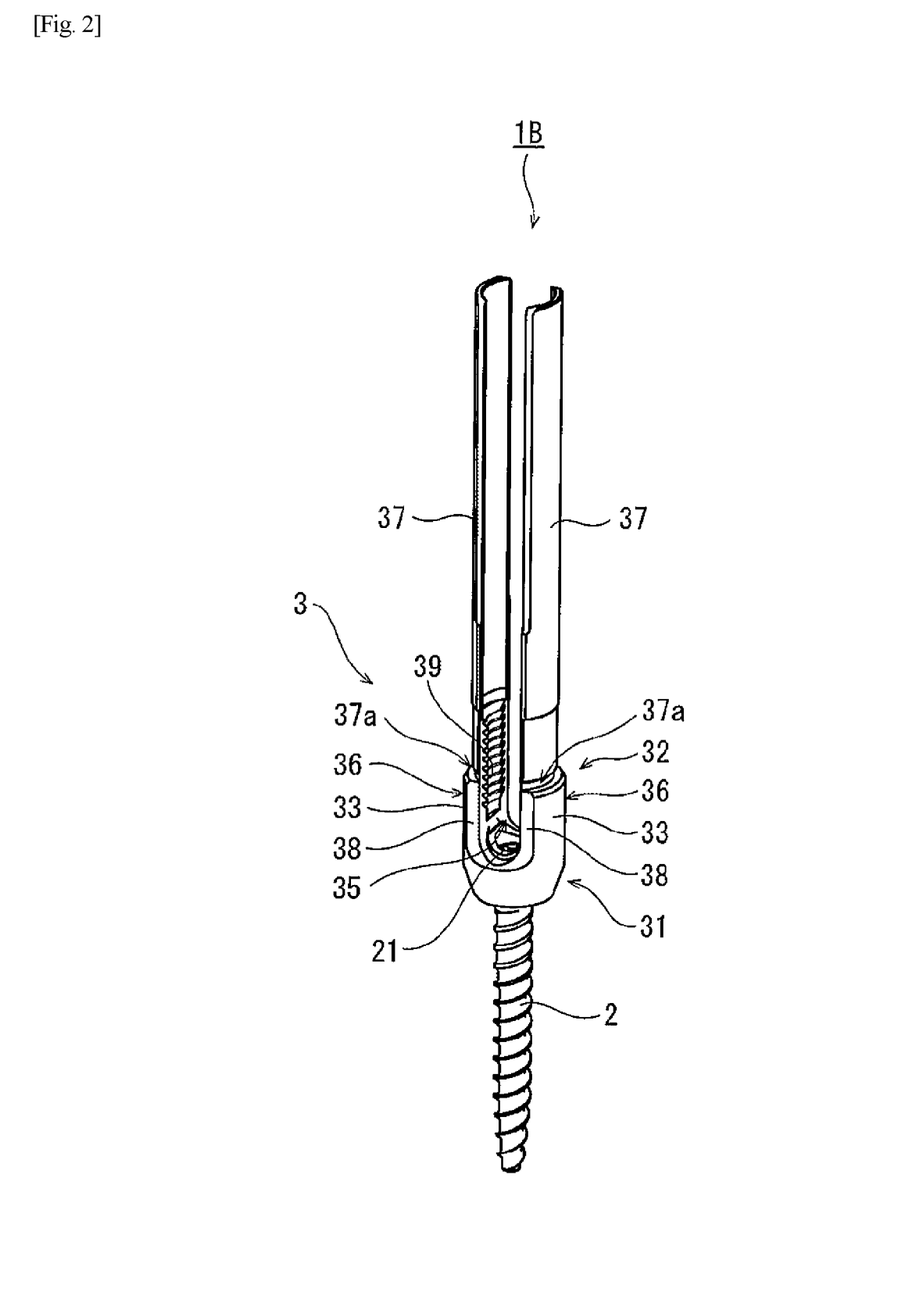
FIG. 2 is a perspective view showing another example of a spinal fixation tool to which a spinal fixation tool holding device according to an embodiment of the present invention can be applied.

FIG. 2 is a perspective view showing another example of a spinal fixation tool to which a spinal fixation tool holding device according to an embodiment of the present invention can be applied. In the example shown in FIG. 2, the same components as those in the example shown in FIG. 1 are denoted by the same reference numerals, and a description of them will be omitted. A spinal fixation tool 1B shown in FIG. 2 differs from the spinal fixation tool 1 shown in FIG. 1 in that the spinal fixation tool 1B has a pair of tab portions 37 extending in the axis line direction from the distal end portion of the upper portion 32 of the head portion 3 in the axis line direction. The pair of tab portions 37 extend upward from the respective upper end portions of the pair of arcuate portions 36. The pair of tab portions 37 have a predetermined inner diameter.

The pair of tab portions 37 each have a length by which it extends outward from the skin (the opening portion of an incised portion) of a subject in a state in which the bone engagement portion 2 is engaged with the bone of the subject, and are configured as a passage for a rod member, set screw, or the like (to be described later) at the time of an operation. The pair of tab portions 37 are formed such that connecting portions 37a for the pair of arcuate portions 36 are thinner than the remaining portions, and the pair of tab portions 37 can be cut from the upper portion 32 by bending the connecting portions 37a. Instead of this, the pair of tab portions 37 are configured so as to allow predetermined extension members to be attached to the outer surfaces of the tab portions. The extension members each have a length by which it extends outward from the skin of the subject while the extension members are attached to the pair of tab portions 37 and the bone engagement portion 2 is engaged with the bone of the subject, and may be configured as a passage for a rod member, set screw, or the like at the time of an operation. In this case, the pair of tab portions 37 may be shorter than when the pair of tab portions 37 alone form a passage for a rod member, set screw, or the like at the time of an operation.

Below is a brief description of spinal fusion surgery using the spinal fixation tool 1B shown in FIG. 2. First, an upper portion of a predetermined portion of the vertebra with which the spinal fixation tool 1B is to be engaged is incised. The range of incision is preferably almost the same (slightly larger) as the projection range of the spinal fixation tool 1B in a plan view (in an axis line direction view), that is, the circular area of the lower portion 31 which defines the maximum diameter. Thereafter, a thread groove corresponding to the thread diameter of the bone engagement portion 2 is formed in the exposed vertebra by using a thread groove forming tool called as a tap or the like.

Thereafter, the spinal fixation tool 1B extends through the formed thread groove of the vertebra through the incised portion. The bone engagement portion 2 of the spinal fixation tool 1B introduced into the body is rotated about the axis line so as to engage the bone engagement portion 2 with the thread groove of the vertebra. Likewise, the bone engagement portions 2 of the plurality of spinal fixation tools 1B are engaged with the thread grooves of the corresponding vertebrae. Thereafter, a rod member 5 is installed so as to straddle a plurality of a pair of slots 35 respectively provided in each of the plurality of spinal fixation tools 1B. When the rod member 5 is introduced into the body, the rod member 5 supported by a predetermined rod member supporting tool is introduced from between the pair of tab portions 37 extending outward from the incised portion for the spinal fixation tool 1B or an incised portion for the insertion of the rod portion at a predetermined distance from the incised portion.

After the rod member 5 is installed between the pair of slots 35, a set screw 6 (see FIG. 7 (described later)) is threadably engaged with a thread groove 39 formed in the inner wall 34 of the upper portion 32 of the head portion 3 to temporarily fix the rod member 5 to the spinal fixation tool 1B. Thereafter, adjustment of the positions of the rod members 5 and adjustment of the distances between the spinal fixation tools 1B as described later are performed. After such adjustment, by rotating the set screw 6 relative to the head portion 3, the set screw 6 is finally fastened to the head portion 3 so as not to allow the rod member 5 to move. In this final fastening operation, the spinal fixation tool holding device according to this embodiment is used as a counter device for holding the head portion 3 with respect to the rotating set screw 6.

Figure 3:
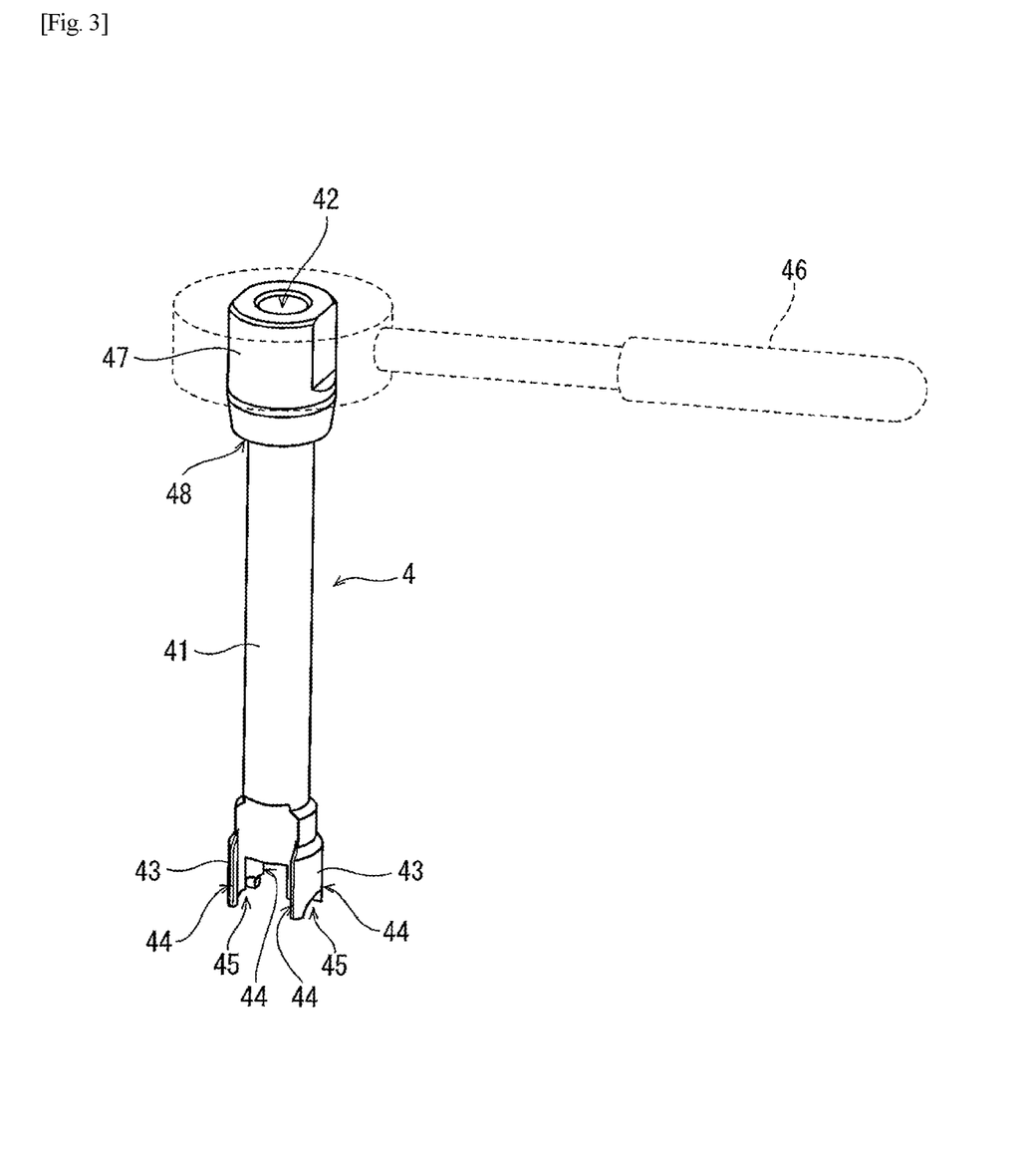
FIG. 3 is a perspective view showing a spinal fixation tool holding device according to an embodiment of the present invention.
Figure 4:
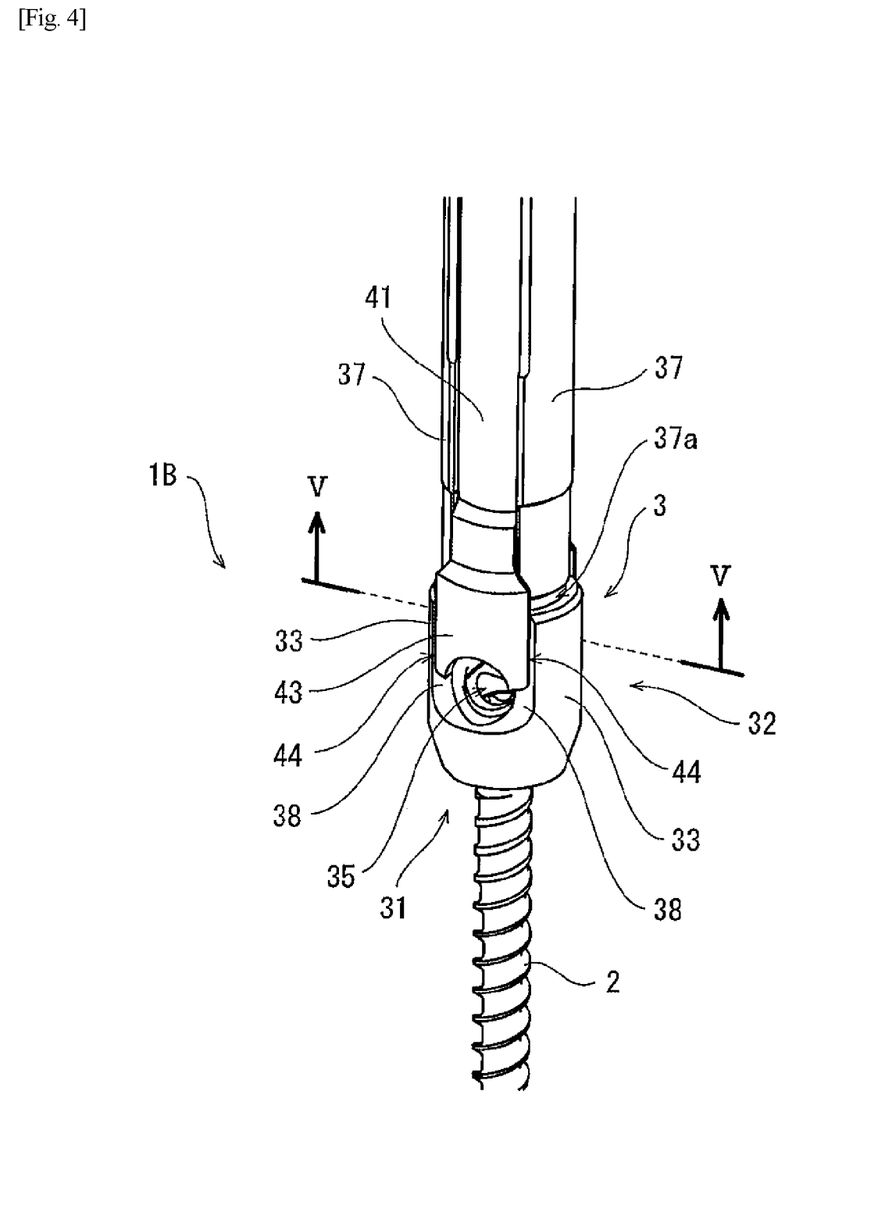
FIG. 4 is an enlarged perspective view showing a portion near to the head portion of the spinal fixation tool in a state in which the spinal fixation tool holding device shown in FIG. 3 is assembled to the spinal fixation tool shown in FIG. 2.

FIG. 3 is a perspective view showing a spinal fixation tool holding device according to one embodiment of the present invention. FIG. 4 is an enlarged perspective view showing a portion near to the head portion of the spinal fixation tool in a state in which the spinal fixation tool holding device shown in FIG. 3 is assembled to the spinal fixation tool shown in FIG. 2. FIG. 4 omits the illustration of the rod member 5. FIG. 5 is a cross-sectional view taken along line V-V shown in FIG. 4. As shown in FIGS. 3 to 5, the spinal fixation tool holding device (to be simply referred to as a holding device hereinafter) 4 according to this embodiment includes a circular cylindrical main body portion 41 having a central axis C0. That is, the main body portion 41 has a hollow portion 42. The above driver can extend through the hollow portion 42. The main body portion 41 has an outer cross-section (outer diameter) equal to or less than a cross-section (inner diameter) defining the inner wall 34 of the upper portion 32 of the spinal fixation tool 1B. The outer diameter of the main body portion 41 is preferably almost equal to or slightly smaller than the inner diameter of the upper portion 32 (that is, the main body portion 41 preferably has a diameter that allows it to be detachably inserted between the inner walls 34 of the upper portion 32 and can minimize the gap between them).

The holding device 4 further includes a pair of locking pieces 43 that protrude outward in the radial direction from the distal end portion (the lower end portion at the time of an operation) of the main body portion 41 in the direction of the central axis C0. The pair of locking pieces 43 protrude outward in the radial direction from the distal end portion of the main body portion 41 in the direction of the central axis C0 at the positions of the pair of slots 35 while the main body portion 41 is positioned within the inner diameter defining the inner walls 34 of the upper portion 32 when the head portion 3 is viewed from the axis line direction. The distal end portion (lower end portions) of the pair of locking pieces 43 in the axis line direction are located below the distal end portion (lower end portion) of the main body portion 41 in the direction of the central axis C0.

The pair of locking pieces 43 have first engagement portions 44 engaged with side walls 38 of the head portion 3 while being positioned within the pair of slots 35. More specifically, the first engagement portions 44 are formed at both end portions of each of the pair of locking pieces 43 in the widthwise direction.

As shown in FIG. 5, each of the pair of locking pieces 43 has a width corresponding to the width of a corresponding one of the pair of slots 35 of the head portion 3. Further, the pair of locking pieces 43 have such a shape that they are contained within the outer shape of the head portion 3 (within the outer circumferential circle C1 defining the maximum diameter) while being positioned within the pair of slots 35. Each side wall 38 of the upper portion 32 (the pair of arcuate portions 36) of the head portion 3 has a first surface 38a along the opposing direction of the pair of slots 35 (the up/down direction on the drawing of FIG. 5) and a second surface 38b orthogonal to the first surface 38a. Each first engagement portion 44 has a shape corresponding to the above side wall 38 of the upper portion 32. That is, the first engagement portion 44 includes a first surface 44a along the opposing direction of the pair of locking pieces 43 and a second surface 44b orthogonal to the first surface 44a. This make it possible to disperse the force that makes the head portion 3 pivot about the axis line in two orthogonal directions when the pair of locking pieces 43 are engaged with the arcuate portions 36 of the head portion 3. It is therefore possible to establish firm engagement with respect to the pivoting movement about the axis line. The holding device 4 is positioned between the pair of tab portions 37 while the first engagement portions 44 are engaged with the side walls 38 of the head portion 3.

As shown in FIG. 3, the holding device 4 includes an attachment mechanism 47 that can attach a handle 46 to the proximal end portion (the upper end portion at the time of an operation) of the main body portion 41 in the axis line direction. The attachment mechanism 47 has a shape that prevents relative rotation of the handle 46 with respect to the holding device 4 about the axis line while the handle 46 is attached. In the example shown in FIG. 3, the attachment mechanism 47 has a shape in which at least a part of the outer surface of the cylindrical member is flattened, and is formed into a structure corresponding to the attachment portion of the corresponding handle 46. The structure of the attachment mechanism 47 is not limited to this, and various known modes such as having a polygonal columnar outer surface can be variously applied. Instead of the structure that allows the handle 46 to be attached to the holding device 4, the handle 46 may be integrally provided on the holding device 4. Furthermore, the holding device 4 has an inner diameter that is concentric with the main body 41 and larger than the outer diameter of the main body 41 at the lower end portion of the attachment mechanism 47, and includes a groove 48 between the outer peripheral surface of the main body portion 41 and the inner circumferential surface of the attachment mechanism 47, through which the pair of tab portions 37 can extend. While the holding device 4 is engaged with the head portion 3, the upper end portions of the pair of tab portions 37 extend through the groove 48 (see FIGS. 6 and 7 to be described later). This makes it possible to prevent the tab portion 37 from being separated from the main body portion 41 of the holding device 4 and being accidentally broken.

As described above, in this embodiment, the spinal fixation system includes the spinal fixation tool 1B as described above and the holding device 4 for holding the spinal fixation tool 1B. According to the above configuration, while the main body portion 41 of the holding device 4 is positioned inside the head portion 3 of the spinal fixation tool 1B, the pair of locking pieces 43 exist at the positions of the pair of slots 35 formed in the head portion 3 so as to protrude outward in the radial direction from the main body portion 41. This engages the engagement portions 44 of the pair of locking pieces 43 are engaged with the head portion 3. At this time, the pair of locking pieces 43 protruding into the pair of slots 35 have such a shape as to be contained in the outer circumferential circle C1 which defines the maximum diameter of the head portion 3 while being positioned within the pair of slots 35.

In the conventional configuration, because the holding device is configured to grip the upper end portion of the head portion 3 from outside, it was impossible to accommodate the holding device in the outer circumferential circle C1 defining the maximum diameter of the head portion 3. Accordingly, in order to use the holding device, it was necessary to incise a range wider than the range required to allow the spinal fixation tool 1B to extend through. In contrast to this, in the holding device 4 according to this embodiment, as described above, the main body portion 41 is located inside the inner wall 34 of the upper portion 32 of the head portion 3, and the engagement portions (the pair of locking pieces 43) for the head portion 3 are arranged so as to protrude from the inside to the outside of the head portion 3.

This prevents the holding device 4 from protruding from the spinal fixation tool 1B when the holding device 4 is engaged with the head portion 3 of the spinal fixation tool 1B to hold the spinal fixation tool 1B. This makes it possible to prevent an increase in the range of invasion (the range of incision) into the human body when the holding device 4 is attached to the spinal fixation tool 1B.

According to this embodiment, both end portions of each of the pair of locking pieces 43 in the widthwise direction are engaged with the portions defining the pair of slots 35 of the head portion 3. This can prevent the head portion 3 of the spinal fixation tool 1B from pivoting in the circumferential direction by holding the holding device 4 with the handle 46 or the like attached to the attachment mechanism 47.

Figure 6:
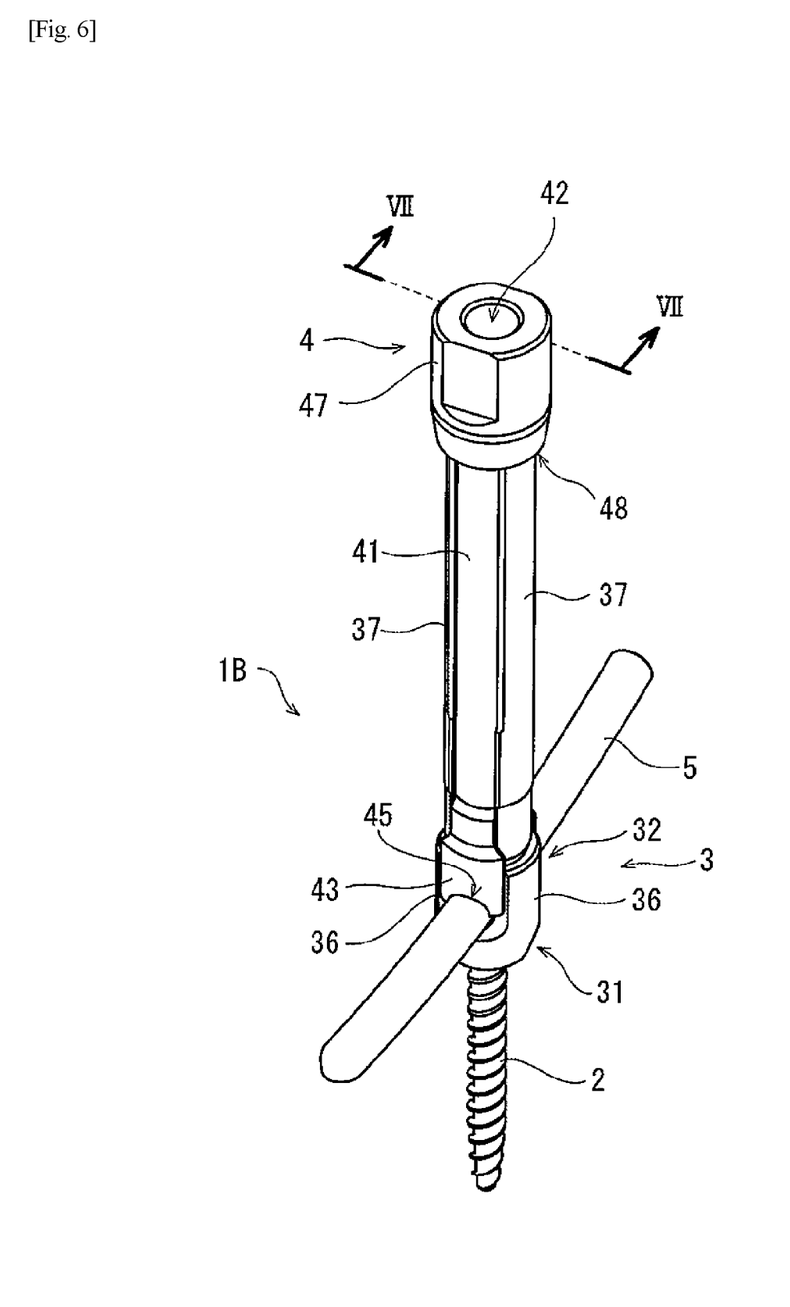
FIG. 6 is a perspective view showing a state in which the spinal fixation tool holding device shown in FIG. 3 is assembled, with the spinal fixation tool shown in FIG. 2 holding the rod member.

In this embodiment, the pair of locking pieces 43 have a second engagement portion 45 engaged with the rod member 5 held in the pair of slots 35 while being positioned within the pair of slots 35. FIG. 6 is a perspective view showing a state in which the spinal fixation tool holding device shown in FIG. 3 is assembled, with the spinal fixation tool shown in FIG. 2 holding the rod member. FIG. 7 is a sectional view taken along line VII-VII shown in FIG. 6. The second engagement portion 45 has an arcuate notch corresponding to the outer diameter of the rod member 5 at the distal end portion of each of the pair of locking pieces 43.

As described above, in spinal fusion surgery using the spinal fixation tool 1B, after each bone engagement portion 2 of the plurality of spinal fixation tools 1B is engaged with the thread groove of the vertebra, the rod member 5 is installed so as to straddle the plurality of the pair of slots 35 provided respectively for the plurality of spinal fixation tools 1B. After the rod member 5 is installed between the plurality of the pair of slots 35, the set screw 6 is threadably engaged with the thread groove 39 formed in the inner wall 34 of the upper portion 32 of the head portion 3.

Figure 7:
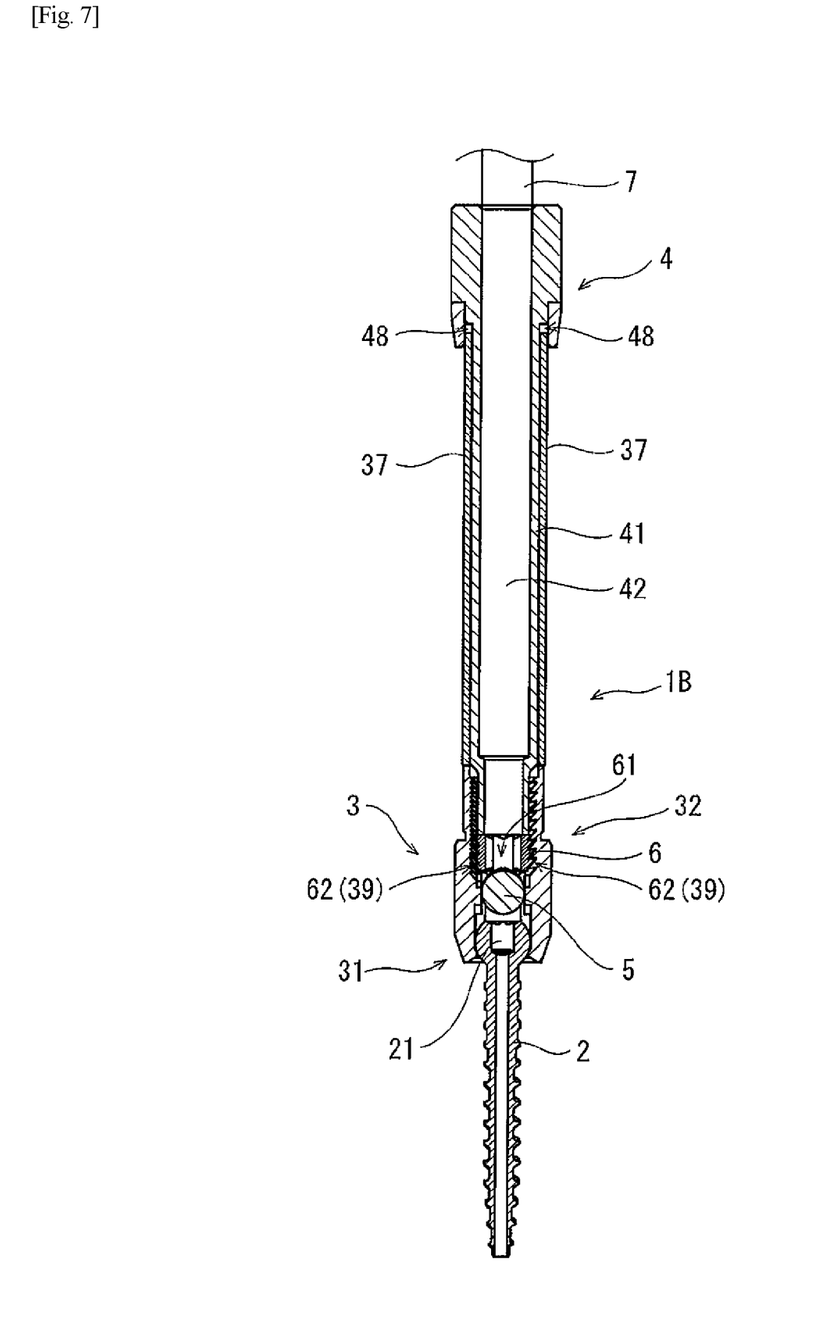
FIG. 7 is a cross-sectional view taken along line VII-VII shown in FIG. 6.

As shown in FIG. 7, the set screw 6 is provided with a driver engagement portion 61 at least on the upper surface and a thread engagement portion 62 on each side face. In this embodiment, the set screw 6 has the driver engagement portion 61 formed as a through hole.

In attaching the set screw 6, the head portion 3 is held by the holding device 4 while the set screw 6 is disposed on the rod member 5. In this case, the second engagement portions 45 formed in the respective distal end portions of the pair of locking pieces 43 are engaged with the rod member 5 held in the pair of slots 35 of the head portion 3. Therefore, holding the holding device 4 while gripping the handle 46 (see FIG. 3) will prevent the spinal fixation tool 1B holding the rod member 5 from pivoting in the circumferential direction. In this embodiment, the first engagement portion 44 is also engaged with the side wall 38 of the upper portion 32 of the head portion 3 while the second engagement portion 45 is engaged with the rod member 5.

In this state, the driver 7 extending through the hollow portion 42 of the holding device 4 is engaged with the driver engagement portion 61 of the set screw 6 to rotate the driver 7 relative to the head portion 3. This makes the set screw 6 be threadably engaged with the thread groove 39 formed in the head portion 3 to fix the rod member 5 installed in the pair of the slots 35.

Figure 8:
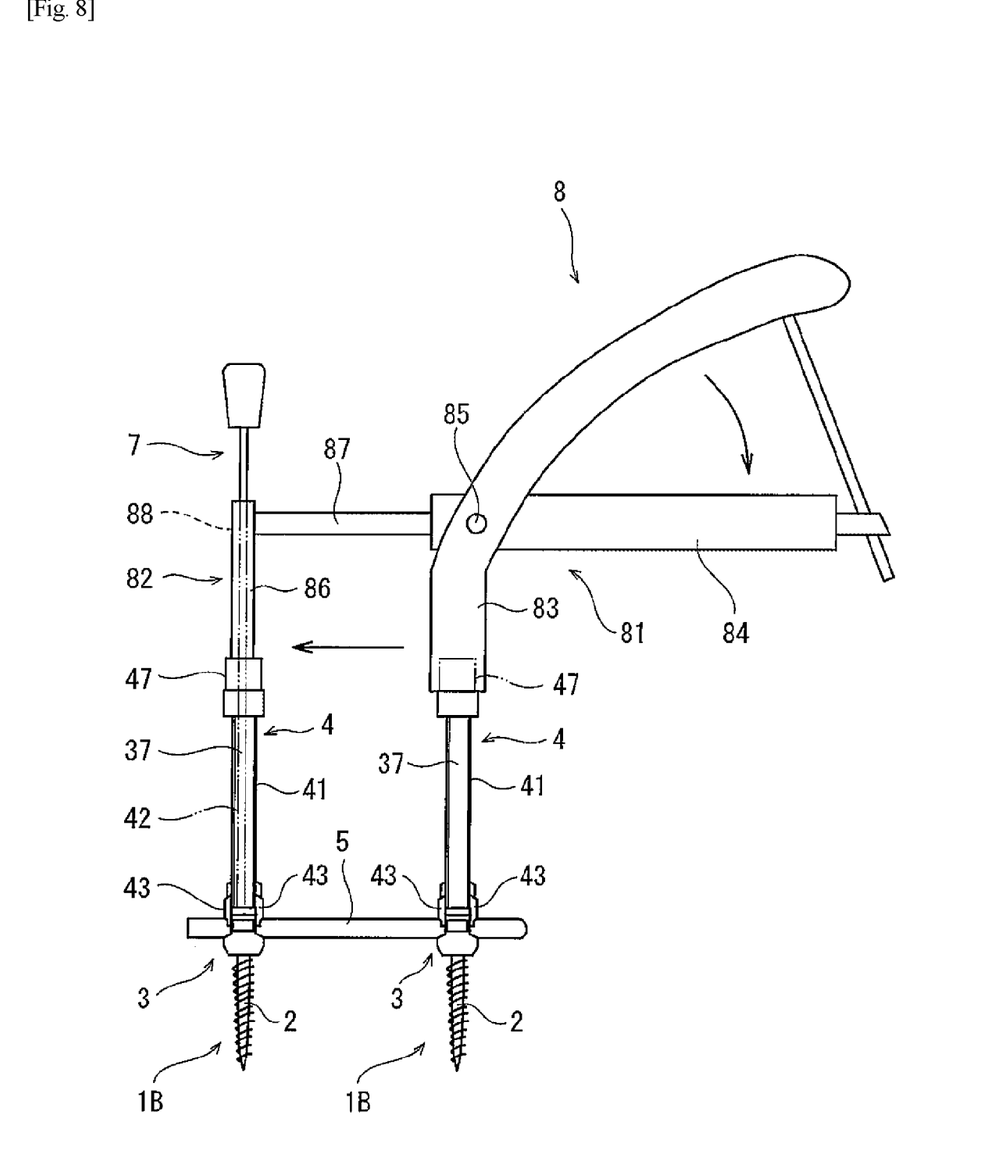
FIG. 8 is a view showing a state in which a compressor is attached to the holding device according to this embodiment.

The holding device 4 according to this embodiment functions not only as a counter device for a driver 7 for fastening the bone engagement portion 2 or the set screw 6 as described above, but also as a base portion to which, for example, a compressor is attached. FIG. 8 is a view showing a state in which a compressor is attached to the holding device according to this embodiment.

A compressor 8 has a structure that acts to reduce the distance between the two spinal fixation tools 1B engaged with the vertebrae. The compressor 8 is provided with a first portion 81 connected to one spinal fixation tool 1B via the holding device 4 and a second portion 82 connected to another spinal fixation tool 1B via the holding device 4. The first portion 81 includes a first grip portion 83 having one end portion engaged with the attachment mechanism 47 of the holding device 4 and the other end portion with a grip portion and a second grip portion 84 having one end portion axially supported by the first grip portion 83 so as to be pivotal around a pivot shaft 85 provided in a direction orthogonal to the axis line direction of the holding device 4 and the other end portion with a grip portion. The second portion 82 includes a cylindrical member 86 having a through hole 88 through which the driver 7 can extend and an extend-through member 87 having one end portion connected to the cylindrical member 86 so as to have an axis line in a direction orthogonal to the axis line direction of the cylindrical member 86 and the other end portion extending through the second grip portion 84.

The second part 82 is connected to the spinal fixation tool 1B by making the driver 7 extend through both the through hole 88 of the cylindrical member 86 and the hollow portion 42 of the holding device 4 engaged with the spinal fixation tool 1B.

According to such a configuration, gripping both the other end portion of the first grip portion 83 and the other end portion of the second grip portion 84 makes them pivot about the pivot shaft 85 in a direction in which they approach. At this time, because the distal end portion of the first grip portion 83 is connected to the holding device 4 engaged with the spinal fixation tool 1B, a force acting between the first grip portion 83 and the second grip portion 84 upon pivoting movement is converted into a force with which the extend-through member 87 extends through the second grip portion 84 (that is, a force in a direction orthogonal to the axis line direction of the spinal fixation tool 1B). This force then acts in a direction to reduce the distance between the first grip portion 83 of the first portion 81 and the cylindrical member 86 of the second portion 82. This makes it possible to reduce the distance between two adjacent spinal fixation tools 1B.

The mode of the compressor 8 described above is not limited to the above, and various known configurations can be applied. In addition, in a mode similar to the above mode, it is also possible to attach and use a distractor to the holding device 4 according to this embodiment such that when the first and second grip portions are gripped, the distractor increases the distance between the two adjacent spinal fixation tools 1B.

Figure 9:
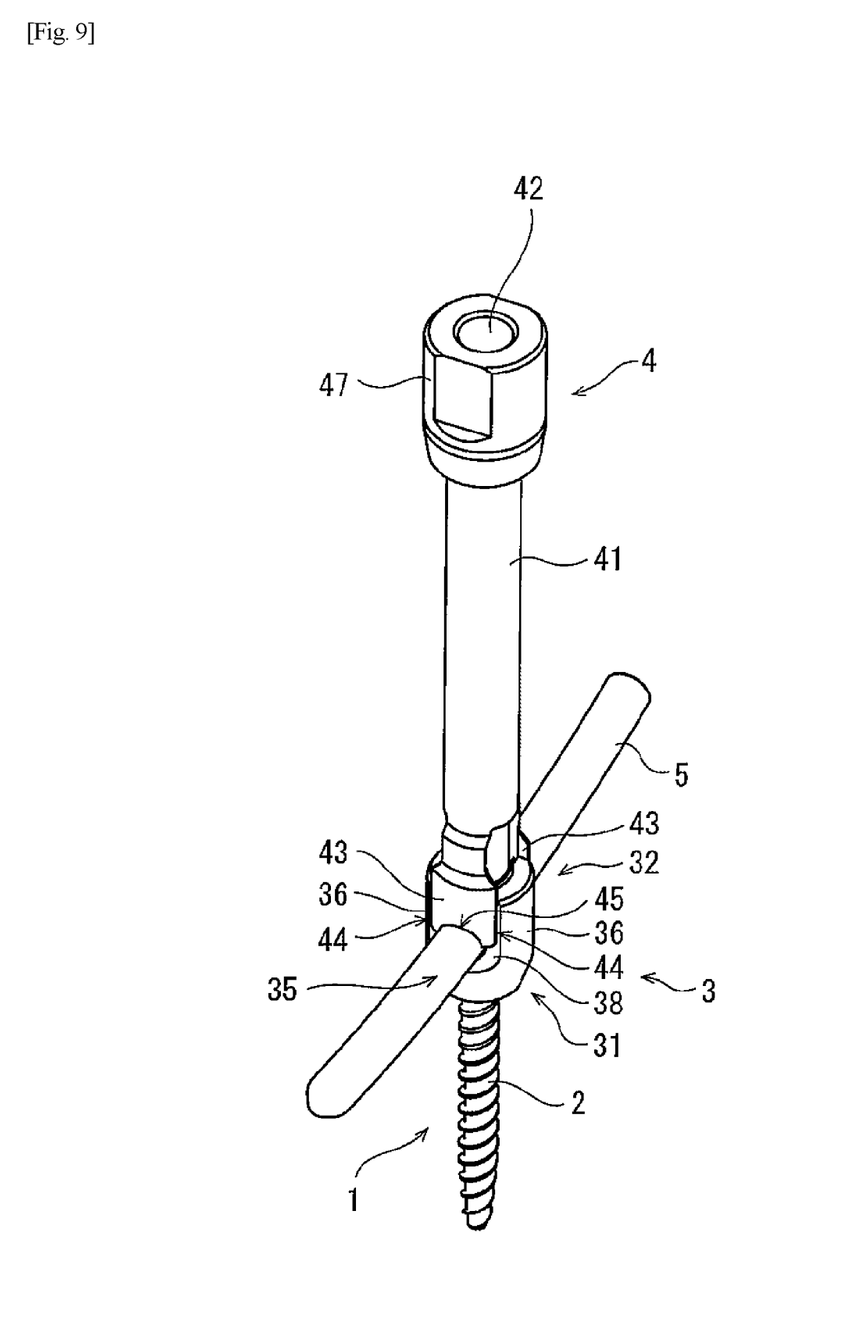
FIG. 9 is a perspective view showing a state in which the spinal fixation tool holding device shown in FIG. 3 is assembled, with the spinal fixation tool shown in FIG. 1 holding the rod member.

The holding device 4 according to this embodiment can also be attached to a spinal fixation tool 1 without a pair of tab portions 37 like that shown in FIG. 1. FIG. 9 is a perspective view showing a state in which the spinal fixation tool holding device shown in FIG. 3 is assembled, with the spinal fixation tool shown in FIG. 1 holding the rod member. As shown in FIG. 9, by extending the pair of locking pieces 43 through the pair of slots 35 of the head portion 3 of even the spinal fixation tool 1 without the pair of tab portions 37, the holding device 4 is engaged with the head portion 3. Referring to FIG. 9, the second engagement portions 45 of the pair of locking pieces 43 are engaged with the rod member 5 held by the head portion 3 to engage the holding device 4 with the head portion 3. However, as in the case shown in FIG. 4, even when the rod member 5 is not disposed, engaging the first engagement portions 44 of the pair of locking pieces 43 with the side walls 38 of the head portion 3 can engage the holding device 4 with the head portion 3.

Although the embodiment of the present invention has been described above, the present invention is not limited to the above embodiment, and various improvements, changes, and modifications can be made without departing from the spirit of the present invention.

For example, in the this embodiment, the pair of locking pieces 43 of the holding device 4 has been described as having both of the first engagement portion 44 and the second engagement portion 45 as engagement portions, but may be configured to include any one of the engagement portion 44 and the second engagement portion 45. For example, when only the first engagement portion 44 is to be provided, any notches need not be provided in the distal end portions of the pair of locking pieces 43. The spinal fixation tool to which the holding device 4 according to this embodiment is applied is not limited to the configuration in which the bone engagement portion 2 is formed by a screw shaft as in the above embodiment, but also includes, for example, a configuration in which the bone engagement portion 2 has a hook shape.

In addition, the shape of the holding device 4, particularly the shape of the pair of locking pieces 43 of the holding device 4 is not limited to the shape shown in the accompanying drawings as long as it does not depart from the spirit of the present invention. For example, in the above embodiment, as described above, the second engagement portion 45 has an arcuate notch corresponding to the outer shape of the rod member 5, but the notch may be formed in any shape other than an arcuate shape, such as a polygonal shape.

The spinal fixation tool held by the holding device 4 as described in this embodiment is not limited to the spinal fixation tools 1 and 1B described in the above embodiment, and can take various forms. For example, in the above embodiment, the set screw 6 is threadably engaged with the thread groove 39 formed in the inner wall 34 of the upper portion 32 of the head portion 3. However, the set screw 6 may be attached to the upper portion 32 of the head portion 3 through intermediate member such as a locking cap. In this case, the inner wall 34 of the upper portion 32 of the head portion 3 is provided with an engagement portion (a concave portion, convex portion, or the like) with such an intermediate member. The intermediate member has a cylindrical shape and has an outer shape so as to be engaged with the engagement portion of the inner wall 34. A thread groove is formed in the inner wall of the intermediate member, and the set screw 6 is configured to be threadably engaged.

The shape of the head portion 3 of the spinal fixation tool is not limited to a circular cylindrical shape as described in the above embodiment as long as it is cylindrical. For example, the head portion 3 may be in the form of a rectangular cylindrical shape having a polygonal cross-section, or may have a peripheral cross-section including curved and linear portions (such as a rectangular cylindrical shape with round corners). The shape of the holding device 4 is not limited to a circular cylindrical shape, and can be a shape conforming to the cross-sectional shape of the head portion 3. In other words, the holding device 4 includes the cylindrical main body portion 41 having an outer cross-section equal to or less than a cross-section defining the inner wall of the upper portion 32 of the head portion 3 and a pair of locking pieces 43 protruding outward from the distal end portion of the main body portion 41 in the direction of the central axis C0 along a direction perpendicular to the central axis C0 at the positions of the pair of slots 35 while the main body portion 41 is positioned within the inner wall 34 of the upper portion 32 when viewed from the direction of the central axis C0. The pair of locking pieces 43 may have such a shape as to be contained within the outer shape of the head portion 41 while being positioned within the pair of slots 35.

INDUSTRIAL APPLICABILITY

The spinal fixation holding device and the spinal fixation system including the same according to the present invention are useful for preventing an increase in the range of invasion into the human body when the holding device is attached to the spinal fixation tool.

REFERENCE SIGNS LIST 1, 1B spinal fixation tool
2 bone engagement portion
3 head portion
4 holding device
5 rod member
31 lower portion
32 upper portion
33 outer wall
34 inner wall
35 slot
36 arcuate portion
37 tab portion
38 side wall
41 main body portion
42 hollow portion
43 locking piece
44 first engagement portion
45 second engagement portion

The invention claimed is:

1. A spinal fixation tool holding device for holding a spinal fixation tool,
the spinal fixation tool including
a bone engagement portion provided at a distal end portion and engaged with a bone, and
a head portion provided at a proximal end portion,
the head portion having
a cylindrical lower portion that holds the bone engagement portion, and
an upper portion extending upward from the lower portion and having an outer wall and an inner wall having an identical central axis to a central axis of an outer shape of the lower portion,
the upper portion having a pair of slots which are opened in a direction perpendicular to the central axis in parts of the outer wall and the inner wall around the central axis,
the holding device comprising:
a cylindrical main body portion having an outer cross-section equal to or less than a cross-section defining the inner wall of the upper portion; and
a pair of locking pieces protruding outward from the distal end portion of the main body portion in the central axis direction along a direction perpendicular to the central axis at the pair of slot positions while the main body portion is positioned within the inner wall of the upper portion when viewed from the central axis direction,
wherein the pair of locking pieces have engagement portions that are engaged with side walls joining the outer wall and the inner wall of the head portion while being positioned inside the pair of slots,
a circular cylindrical portion forming an outer periphery of the lower portion includes an outer circumferential circle that defines a maximum diameter of the head portion, and
the pair of locking pieces each has an arcuate shape extending along the outer circumferential circle, which defines the maximum diameter of the head portion, while being positioned within the pair of slots.

2. The spinal fixation tool holding device according to claim 1, wherein the engagement portions are formed on both end portions of each of the pair of locking pieces in a widthwise direction, and each of the pair of the locking pieces has a width corresponding to a width of each of the pair of slots of the head portion.

3. The spinal fixation tool holding device according to claim 1, wherein the engagement portion has an arcuate notch corresponding to an outer diameter of a rod member held by the pair of slots at a distal end portion of each of the pair of locking pieces.

4. The spinal fixation tool holding device according to claim 1, wherein the spinal fixation tool has a pair of tab portions extending in a central axis direction from a distal end portion of the upper portion of the head portion in the central axis direction, and the holding device is positioned between the pair of tab portions in a state where the pair of the locking pieces are engaged with the side wall of the head portion.

5. A spinal fixation system comprising a spinal fixation tool and a spinal fixation holding device for holding the spinal fixation tool, wherein
the spinal fixation tool includes
a bone engagement portion provided at a distal end portion and engaged with a bone, and
a head portion provided at a proximal end portion,
the head portion has
a cylindrical lower portion that holds the bone engagement portion, and
an upper portion extending upward from the lower portion and having an outer wall and an inner wall having an identical central axis to a central axis of an outer shape of the lower portion,
the upper portion having a pair of slots which are opened in a direction perpendicular to the central axis in parts of the outer wall and the inner wall around the central axis,
the holding device includes a cylindrical main body portion having an outer cross-section equal to or less than a cross-section defining the inner wall of the upper portion, and a pair of locking pieces protruding outward from the distal end portion of the main body portion in the central axis direction along a direction perpendicular to the central axis at the pair of slot positions while the main body portion is positioned within the inner wall of the upper portion when viewed from the central axis direction, the pair of locking pieces have engagement portions that are engaged with side walls joining the outer wall and the inner wall of the head portion while being positioned inside the pair of slots, a circular cylindrical portion forming an outer periphery of the lower portion includes an outer circumferential circle that defines a maximum diameter of the head portion, and the pair of locking pieces each has an arcuate shape extending along the outer circumferential circle, which defines the maximum diameter of the head portion, while being positioned within the pair of slots.

\* \* \* \* \*